United States Patent
Deckner

Patent Number: 5,891,148
Date of Patent: Apr. 6, 1999

[54] INVERSE HELICAL REAMER

[76] Inventor: André Georges Deckner, 5 Rue de l'Harmonie, 75015 Paris, France

[21] Appl. No.: 792,874

[22] Filed: Jan. 31, 1997

[30] Foreign Application Priority Data

Feb. 8, 1996 [FR] France ................................... 96 01540

[51] Int. Cl.⁶ .................................................. A61B 17/56
[52] U.S. Cl. ............................................................... 606/80
[58] Field of Search ..................... 408/199, 210, 408/250; 606/80, 79, 180

[56] References Cited

U.S. PATENT DOCUMENTS

| 26,613 | 12/1859 | Phelps | 408/210 |
|---|---|---|---|
| 324,763 | 8/1885 | Foster | 408/210 |
| 770,480 | 9/1904 | Stanger | 408/210 |
| 3,051,205 | 8/1962 | Kallio | 408/210 |
| 3,824,026 | 7/1974 | Gasskins | 408/210 |
| 4,725,171 | 2/1988 | DeTorre | 408/213 |
| 4,751,922 | 6/1988 | DePietropolo | 606/80 |
| 4,830,000 | 5/1989 | Shutt | 606/80 |
| 5,562,673 | 10/1996 | Koblish et al. | 606/80 |

FOREIGN PATENT DOCUMENTS

| 0 330 107 | 8/1989 | European Pat. Off. . |
|---|---|---|
| 25 42 056 | 3/1977 | Germany . |

Primary Examiner—Guy V. Tucker
Attorney, Agent, or Firm—Pearne, Gordon, McCoy & Granger LLP

[57] ABSTRACT

This inverse reamer is formed of a tang extended by a helical shank. The edge turned towards the point is cutting and is wound in a direction contrary to the direction of rotation normally provided for operating the reamer.

18 Claims, 1 Drawing Sheet

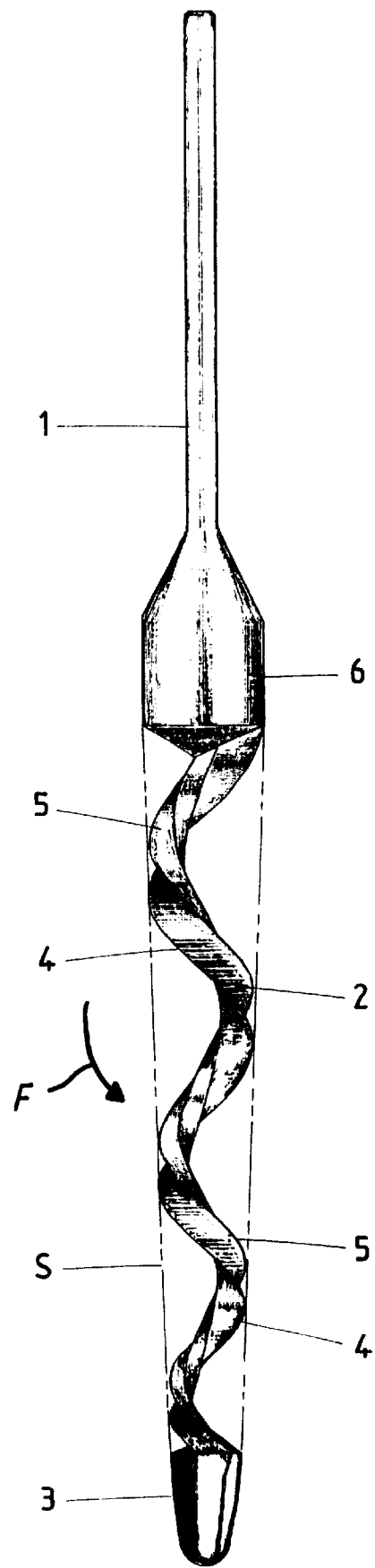

INVERSE HELICAL REAMER

BACKGROUND OF THE INVENTION

The present invention concerns a helical reamer intended in particular to give the desired shape to the medullary cavity of a hollow bone.

The cavity intended to be given a conical shape must pre-exist or must be previously created with a traditional drilling instrument, since the main function of the reamer of the present invention is not to drill a hole.

A drill bit is already known which has the disadvantage of penetrating the side face of the bone when the medullary cavity is curved inwards. If the point of the bit is rounded, so as to prevent any perforation, the bit can jam and the bone can break.

The invention overcomes these disadvantages by means of a reamer having a high degree of safety, which can follow the curve of a medullary cavity while remaining centered.

SUMMARY OF THE INVENTION

The invention concerns a reamer formed of a tang extended by a shank having a substantially helical shape ending in a point on the opposite side to the tang and having an edge turned towards the point characterized in that the shank takes the form of a single flexible blade wound into a helix about an imaginary axis, at least part of the edge turned towards the point is cutting and the direction in which the helix is wound is opposite to the direction of rotation normally provided for operating the reamer, the point comprises at least one part having a continuously circular cross-section perpendicular to the imaginary axis, and the tang comprises a boss of which at least part of the transverse section is continuously circular and has a radius equal to or greater than the largest radius vector of the helix.

The inverse reamer according to the invention has the important property of not having the tendency to progress on its own within the cavity during preparation. When it is driven in rotation and produces friction on the cavity, it automatically tends to withdraw. It only progresses if the operator exerts a high axial thrust and cutting ceases as soon as this thrust ceases. It does not jam since it automatically has the tendency to withdraw. In addition, it is made flexible since it consists of a single blade and hence is introduced more easily into an inwardly curving medullary cavity. In spite of its flexibility, it remains well centered by the boss and by the point.

The usual direction in which a spiral constituting normal drilling instruments is wound may be defined as follows: for an observer situated on the tang side of the instrument and away from the point, the constitutive spiral is wound in a clockwise direction as it passes away from the tang in the direction of the point.

The inverse reamer according to the present invention differs substantially from normal drilling instruments in that the spiral of which the instrument consists is wound in an anticlockwise direction under the conditions of observation in the preceding paragraph.

During use, the usual direction of rotation of drilling instruments may be stated as follows: if the observer is situated at the tang end of the instrument and away from the point, the instrument turns in a clockwise direction.

The inverse reamer according to the present invention is also designed to turn normally in a clockwise direction, under the same observation conditions (right-turning).

A preferred embodiment of the invention consists of giving the point of the instrument a rounded and polished form. This rounding is designed to guide the point of the instrument inside the pre-existing cavity without it binding against, damaging or especially piercing the inner surface encountered, even if the latter is irregular.

According to a preferred embodiment of the invention, the part of the reamer which comprises the cutting edge is flexible.

This relative flexibility of the instrument also enables the latter to be introduced into pre-existing hollow bodies, the inner channel of which does not have a straight axis, but curves slightly inwards.

An improvement is made to the invention when the tangent at any point of the cutting edge makes a substantially constant angle in space with the axis of the shank. The desired objective to be achieved by having a substantially constant angle between the cutter and the material (bone) to be cut to size is a good distribution of the cutting effect over all the surface to be cut to size.

The cutting edge may be given the form substantially of a three-dimensional logarithmic spiral which possesses simultaneously the property of being inscribed on a conical surface of revolution, the tangent at any point forming a constant angle in space with the axis.

A form of the flat logarithmic spiral is:

$R = e^{k\theta}$ where

R is the radius vector or distance between the "asymptotic pole" of the curve and the running point of the curve, e is the base of Napierian logarithms, equal to approximately 2.718280, θ (theta) is the parameter of the function and represents the angle between one of the axes of the plane and the radius vector, and K is a calculated constant specifying the curve and defining, among others, the angle of the tangent at any point.

For a three-dimensional logarithmic spiral, the third dimension, which in the case of the reamer of the present invention corresponds to the longitudinal axis, may be governed by the form:

$Z = e^{L\theta}$ where

Z is the projection of the running point of the curve onto the longitudinal axis and L is a constant on which the number of turns of the cutter depends.

The desired effect for a reamer according to the invention, the configuration of which substantially follows the preceding formula and the thicknesses and cross-sections of which are calculated as a consequence of this, is a regularly progressive elasticity, giving greater rigidity towards the tang and more elasticity towards the point.

This configuration aims at an optimum adaptation to the curvature of a bone cavity, with a view to implanting a prosthetic pin which curves inwards, and in particular curves inwards according to an appropriate logarithmic spiral.

The previously described properties make it possible, for the present invention, to seek to obtain a reamed cavity having the configuration of a truncated cone, the longitudinal axis of which would not be straight but curvilinear, enabling an implant, which also possesses a shape which is partially that of a truncated cone and which curves inwards on a suitable inwardly curvilinear axis, to be self-locking within this cavity.

In general, it is better for the imaginary enveloping surface of the shank to widen out from the point towards the tang, which assists in preventing the prosthesis from being forced too far into the medullary cavity after its insertion.

According to a variant, the helical pitch of the cutting edge is constant.

According to another variant, the point has cutting edges enabling the reamer to make the entry hole into the bone itself and to create a conical bore in a single operation.

The invention also concerns a process for shaping the medullary cavity of a hollow bone which consists of turning a reamer according to the invention inside the cavity.

BRIEF DESCRIPTION OF THE DRAWING

In the accompanying drawing, given solely by way of example, FIG. 1 is a perspective view of a reamer according to the invention in a version which may be used in the field of bone surgery, for preparing the osseous bed of a damaged bone so as to be able to anchor a prosthesis deeply within an area of the bone which is still healthy.

DESCRIPTION OF THE PREFERRED EMBODIMENT

The reamer consists of a tang (1) designed to be attached, by any suitable means, to a rotating machine, and a metal shank (2) coming from the tang (1). The shank (2) is a flexible blade twisted into a helix.

The blade comprises two edges (4 and 5), one (4) referred to as the front edge which is turned towards the point (3) of the blade, and the other (5) referred to as the rear edge which is turned towards the tang (1). All the edge (4) is cutting, whereas the edge (5) is not cutting. The direction of rotation normally provided for operating the reamer is right-turning. The helix which constitutes the shank (2) turns to the left in an anticlockwise direction as shown by the arrow F. The helical pitch is constant.

The point (3) is rounded which, coupled with the structure of the blade, helps to ensure that the point (3) of the blade cannot pierce the channel of the hollow body into which the reamer is introduced. The point (3) comprises a part with a transverse section perpendicular to the imaginary axis of the reamer, which passes through the axis of the tang (1) and is continuously circular, and the tang has a boss (6) with a radius equal to or greater than the largest radius vector of the helix.

The helix, in FIG. 1, has a step which increases from the point (3) towards the tang (1).

The curve followed by the front cutting edge (4) is a logarithmic spiral. The imaginary enveloping surface (S) of the shank (2) is in the form of a truncated cone widening out from the point (3) towards the tang (1).

The point (3) comprises two cutting edges.

The reamer may be made of metal or ceramic.

I claim:

1. Reamer formed of a tang extended by a shank having a substantially helical shape ending in a point on the opposite side to the tang and having an edge turned towards the point, wherein:

the shank consists essentially of a single flexible blade wound into a helix about an imaginary axis, at least the part of the edge turned towards the point is cutting and the direction in which the helix is wound is opposite to the direction of rotation normally provided for operating the reamer, the point comprises at least one part having a continuously circular cross-section perpendicular to the imaginary axis, and the tang comprises a boss, of which at least part of, the transverse section is continuously and non-helical and said continuously circular part has a radius equal to or greater than the largest radius vector of the helix.

2. Reamer according to claim 1, wherein the edge turned towards the point is cutting.

3. Reamer according to claim 2, wherein the imaginary enveloping surface of the shank widens out from the point towards the tang.

4. Reamer according to claim 3, wherein the enveloping surface is a truncated cone.

5. Reamer according to claim 1, wherein an imaginary enveloping surface of the shank widens out from the point towards the tang.

6. Reamer according to claim 5, wherein the enveloping surface is a truncated cone.

7. Reamer according to claim 1, wherein the tangent at any point of the cutting edge makes a constant angle in space with the axis of the shank.

8. Reamer according to claim 7, wherein the cutting edge of the shank describes a three-dimensional logarithmic spiral.

9. Reamer according to claim 1, wherein the helical pitch of the cutting edge is substantially constant.

10. Reamer according to claim 1, the point of which is rounded.

11. Reamer according to claim 1, wherein the enveloping surface is a truncated cone.

12. Reamer according to claim 1, wherein said single blade has an elongate ribbon shape disposed in spaced relationship about said imaginary axis in said helical shape along said shank.

13. Reamer according to claim 12, wherein said single blade ribbon shape includes a thickness dimension and a width dimension respectively extending between first and second pairs of opposed surfaces, said width dimension being substantially greater than said thickness dimension, and said opposed surfaces providing said blade with a generally rectangular cross section.

14. Reamer according to claim 13, wherein said single blade also includes a length dimension that is substantially greater than said width dimension, and said blade extends from said tang to said point along said length dimension in said helical shape.

15. Reamer according to claim 14, wherein said edge is formed by the intersection of one of each of said first and second surfaces along the length dimension of said blade between said tang and said point.

16. Reamer according to claim 1, wherein said single blade has an elongate ribbon shape including a width, a thickness and a length, said single blade being twisted in said helical shape along said blade length and extending in spaced relationship about said imaginary axis between said tang and said point.

17. Reamer according to claim 16, wherein said single blade includes first and second pairs of opposed surfaces respectively extending along said width and said thickness, and said opposed surfaces provide said blade with a generally rectangular cross section.

18. Reamer according to claim 17, wherein said edge is formed by the intersection of one of each of said first and second surfaces along the length of said blade extending between said tang and said point.

* * * * *